United States Patent [19]
Rothstein

[11] Patent Number: 6,153,381
[45] Date of Patent: Nov. 28, 2000

[54] SCREENING FOR ANTIBIOTICS

[75] Inventor: David M. Rothstein, Lexington, Mass.

[73] Assignee: Millennium Pharmaceuticals, Inc., Cambridge, Mass.

[21] Appl. No.: 08/919,535

[22] Filed: Aug. 28, 1997

[51] Int. Cl.[7] .................................................. C12Q 1/68
[52] U.S. Cl. ........................... 435/6; 435/7.1; 435/7.32; 435/7.4; 435/18; 435/19; 435/24; 435/32; 435/69.1; 435/69.8; 435/172.1; 435/172.3; 435/183; 435/243; 536/24.3; 536/24.32
[58] Field of Search ............................... 435/7.1, 7.4, 18, 435/19, 24, 6, 32, 7.32, 69.1, 69.8, 183, 172.1, 172.3, 243; 536/24.3, 24.32

[56] References Cited

U.S. PATENT DOCUMENTS

| | | | |
|---|---|---|---|
| 4,381,343 | 4/1983 | Citri | 435/24 |
| 4,596,768 | 6/1986 | Singh et al. | 435/7 |
| 5,268,463 | 12/1993 | Jefferson | 536/23.7 |
| 5,830,457 | 11/1998 | Gicquel et al. | 424/93.2 |

OTHER PUBLICATIONS

Cruse et al. *Illustrated Dictionary of Immunology*. Library of Congress Publishers. CRC Publishers, Boca Raton. 1995. p. 219 only.

Frobisher. *Fundamentals of Microbiology* 8th Ed. WB.Saunders Co. Philadelphia. 1968. pp. 290 and 293.

Alberts et al. *Molecular Biology of the Cell*. Garland Publishing, Inc. New York, 1983, pp. 181 and 182.

Aoki et al., "Nocardicin A, a new Monocyclic β–Lactam Antibiotic," *J. Antibiotics*, 29:492–500, 1976.

Aoki et al., "Screening of New and Novel β–Lactam Antibiotics," *Japanese J. Antibiotics*, 30(Suppl.):S–207–S–217, 1977.

Brown et al., "Naturally–Occurring β–Lactamase Inhibitors with Antibacterial Activity," *J. Antibiotics*, 29(6):668–669, 1976.

Charnas et al., "Chemical Studies on the Inactivation of *Escherichia coli* RTEM β–Lactamase by Clavulanic Acid," *Biochemistry*, 78:2185–2189, 1978.

Gadebusch et al., "The Discovery of Cell Wall Active Antibacterial Antibiotics," *Critical Reviews in Biotechnology*, 12(3):225–243, 1992.

Ikeda et al., "Nucleotide sequence involving murG and murC in the mra gene cluster region of *Escherichia coli*," *Nucleic Acids Research*, 18(13):4014, 1990.

Ikeda et al., "The *Escherichia coli* mraY Gene Encoding UDP–N–Acetylmuramoyl–Pentapeptide:Undecaprenyl–Phosphate Phospho–N–Acetylmuramoyl–Pentapeptide Transferase," *J. Bacteriol.*, 173(3):1021–1026, 1991.

Jacobs et al., "Bacterial cell wall recycling provides cytosolic muropeptides as effectors of β–lactamse induction," *EMBO J.*, 13(19):4684–4694, 1994.

Jacobs et al., "AmpD, essential for both β–lactamase regulation and cell wall recycling, is a novel cytosolic N–acetyl-muramyl–L–alanine amidase," *Mol. Microbiol.*, 15(3):553–559, 1995.

Kato et al., "PB–5266 A, B and C, New Monobactams," *J. Antibiotics*, 40(2):135–138, 1987.

Labischinski and Maidhof, "Bacterial peptidoglycan: overview and evolving concepts," *Bacterial Cell Wall, New Comprehensive Biochemistry*, chapter 2, 27:23–37, 1994.

Lindberg et al., "Regulatory components in Citrobacter freundii ampC β–lactamase induction," *Proc. Natl. Acad. Sci. USA*, 82:4620–4624, 1985.

Lugtenberg and van Schijndel–van Dam, "Temperature–Sensitive Mutants of *Escherichia coli* K–12 with Low Activity of the Diaminopimelic Acid Adding Enzyme," *J. Bacteriol.*, 110(1):41–46, 1972.

Matsuhashi, "Utilization of lipid–linked precursors and the formation of peptidoglycan in the process of cell growth . . . ," *Bacterial Cell Wall, New Comprehensive Biochemistry*, chapter 4, 27:55–71, 1994.

Mengin–Lecreulx and Heijenoort, "Nucleotide sequence of the murD gene encoding the UDP–MurNAc–L–Ala–D–Glu synthetase of *Escherichia coli*," *Nucleic Acids Research*, 18(1):183, 1990.

Mengin–Lecreulx et al., The murG Gene of *E. coli* Codes for the . . . N–Acetylglucoseamine Transferase Involved in the Membrane Steps of Peptidoglycan Synthesis, *J. Bacteriol.*, 173(15):4625–4636, 1991.

Michaud et al., "Revised interpretation of the sequence containing the murE gene encoding the UDP–N–acetyl–muramyl–tripeptide synthetase of *E. coli*," *Biochem. J.*, 269:277–280, 1990.

Miyakawa et al., "Cell Wall Peptidoglycan Mutants of E. coli K–12: Existence of Two Clusters of Genes, mra and mrb, for Cell Wall Peptidoglycan Biosynthesis," *J. Bacteriol.*, 112(2):950–958, 1972.

Normark, "Genetics of a chain–forming mutant of *Escherichia coli*," *Genet. Res., Camb.*, 16:63–78, 1970.

Okamura et al., "PS–5, a New β–Lactam Antibiotic from Streptomyces," *J. Antibiotics*, 31(5):480–482, 1978.

Park, "Why does *Escherichia coli* recycle its cell wall peptides?" *Mol. Microbiol.*, 17(3):421–426, 1995.

Parquet et al., "Nucleotide sequence of the murF gene encoding the UDP–MurNAc–pentapeptide synthetase of *Escherichia coli*," *Nucleic Acids Research*, 17(13):5379, 1989.

(List continued on next page.)

*Primary Examiner*—Jennifer Graser
*Attorney, Agent, or Firm*—Fish & Richardson P.C.

[57] ABSTRACT

Assays for the detection of β-lactamase induction can be used to identify compounds that kill bacteria (i.e., bacteriocidal activity) or inhibit bacterial growth (i.e., bacteriostatic activity). The β-lactamase can be encoded, for example, by a β-lactamase gene carried by a bacterial host. The identified compounds can be use to treat bacterial infections in organisms such as mammals. The new methods can be used, for example, for high throughput screening of libraries of potential inhibitors.

20 Claims, 4 Drawing Sheets

OTHER PUBLICATIONS

Starkova et al., "Morphological Mutants of *Escherichia coli*: Nature of the Permeability Barrier in mon and envC Cells," *Ann. Microbiol. (Inst. Past.)*, 129 A(3):265–284, 1978.

Sykes et al., "Moncyclic β–lactam antibiotics produced by bacteria," *Nature*, 291:489–491, 1981.

van Heijenoort, "Murein Synthesis," *Escherichia coli and Salmonella, Cellular and Molecular Biology*, 2nd. ed., chapter 68, pp. 1025–1034, 1996.

van Heijenoort, "Biosynthesis of the bacterial peptidoglycan unit," *Bacterial Cell Wall, New Comprehensive Biochemistry*, chapter 3, 27:39–53, 1994.

SCREENING FOR ANTIBIOTICS

BACKGROUND OF THE INVENTION

The invention relates to methods for identifying compounds that kill bacteria or inhibit bacterial growth. The invention also relates to methods for identifying compounds that can be used to treat infections (e.g., bacterial infections in organisms such as mammals).

Bacterial cell wall peptidoglycan biosynthesis is a multi-step process (see FIG. 1). Although there is some variation between bacterial species, each step in the respective synthetic pathways is essential for the growth of the bacteria. Inhibition of any step can be lethal, and each step is therefore a potential target against which new antibacterial drugs are sought. Inhibitors are already known for some steps in the biosynthetic pathway; however, bacteria have developed resistance to many of these inhibitors, thus necessitating continued searching for new antibacterial agents.

One mode of defense that gram positive bacteria use to resist a certain class of antibacterial agents (i.e., the β-lactams, which inhibit peptidoglycan formation) is to produce an enzyme called β-lactamase. Production of β-lactamase is induced in some bacterial strains by the presence of β-lactams in the cell. β-Lactamase reacts with β-lactam drugs (e.g., penicillin or cephalosporin), rendering the drugs inactive. Certain species of gram negative bacteria such as Enterobacter (e.g., *E. cloacae, E. kobei, E. agglomerans*, or *E. flavus*) and *Citrobacter freundii* also produce β-lactamase, in response to the build-up of cell wall degradation products, not just in the presence of β-lactams per se. Because bacterial cell walls are continuously degraded and reassembled throughout the life cycle of a bacterium, the build-up of degradation products can be due to inhibition of at least one step in the peptidoglycan biosynthetic pathway.

SUMMARY OF THE INVENTION

The invention features new assays based on the discovery that induction of the β-lactamase gene can be used to identify compounds that kill bacteria (i.e., bacteriocidal activity) or inhibit bacterial growth (i.e., bacteriostatic activity), and thus to treat bacterial infections (i.e., to reduce symptoms of existing infections and to prevent infections) in organisms such as mammals. The β-lactamase can be encoded, for example, by a β-lactamase gene normally carried by a bacterial host, or inserted into a host, e.g., a heterologous host. The new methods are highly efficient and sensitive, and can be used, for example, for high throughput screening of libraries of potential inhibitors.

In one embodiment, the invention features a method for identifying a candidate compound (e.g., a single compound or a member of a library of potential inhibitors) that inhibits bacterial growth. The method includes the steps of contacting bacteria with the candidate compound to form a reaction mixture, and then assaying the reaction mixture for induction of β-lactamase, which indicates inhibition of bacterial growth.

The assaying step can, for example, include measuring the optical absorbance (e.g., optical density (OD)) of the reaction mixture (e.g., to detect the absorbance of β-lactamase at 490 nm); detecting the binding of antibodies to β-lactamase; or probing for β-lactamase mRNA.

In this context, a "candidate compound" is any compound not previously known to inhibit "bacterial growth," which includes proliferation of bacteria, budding, cell division, endospore formation, and other forms of reproduction. "Inhibitors of bacterial growth" include both compounds that prevent growth of bacteria (i.e., bacteriostatic compounds) and compounds that kill bacteria (i.e., bacteriocidal compounds).

The invention also features a method for identifying an inhibitor of cell wall biosynthesis. The method includes the steps of contacting bacteria with a candidate compound to form a reaction mixture; and assaying the reaction mixture for induction of β-lactamase, wherein induction of β-lactamase indicates that the candidate compound is an inhibitor of cell wall biosynthesis.

In another embodiment, the invention features a method for identifying a candidate compound that can be used to treat infection in an organism by a bacteria. The method includes the steps of contacting the bacteria with the candidate compound to form a reaction mixture, and then assaying the reaction mixture for induction of β-lactamase, which indicates that the candidate compound can be used to treat bacterial infection.

Organisms that can be treated include mammals (e.g., humans, non-human primates, horses, cows, pigs, sheep, goats, dogs, and cats); non-mammalian animals (e.g., chickens or frogs); other eukaryotes (e.g., plants); and prokaryotes.

The invention also features a method for identifying a candidate compound that inhibits bacterial growth. The method includes the steps of providing bacteria carrying a gene that encodes β-lactamase; incubating the bacteria with the candidate compound under conditions that enable cell wall biosynthesis to form a reaction mixture; and assaying for induction of β-lactamase, which indicates that the candidate compound is an inhibitor of bacterial growth.

A bacteria "carrying a gene" is a bacteria that contains a plasmid, cosmid, vector, or other nucleic acid molecule that includes the gene. The gene can be incorporated into a chromosome (e.g., integrated into a bacterial chromosome) or can be extrachromosomal, but still within the bacterial cell. The gene can be from the same bacterial species as the host, e.g., preexisting in the host, or from a different species (i.e., heterologous). The gene can be a β-lactamase gene from a bacterial species selected from the group of genera consisting of Citrobacter, Enterobacter, Serratia, Pseudomonas, and Proteus. For example, the gene can be ampC from *Citrobacter freundii*. The gene can also include a reporter gene such as lacZ or luc. The reporter gene can be fused to the β-lactamase gene or otherwise under the control of the same regulators as β-lactamase.

The method can also include the steps of obtaining a cell extract containing enzymes, cofactors, and carrier molecules necessary for a particular step or steps of cell wall biosynthesis; supplying a substrate for the step or steps; incubating the candidate compound with the cell extract and the substrate under conditions that enable the step or steps to proceed to form an incubation mixture; and assaying the incubation mixture for the substrate and the product produced in the step or steps. The production of an amount of product less than that normally produced in the step or steps relative to the amount of substrate indicates the presence of an inhibitor of the step or steps.

In addition, the invention features a method for identifying an inhibitor of a particular step or steps of cell wall biosynthesis. The method includes the steps of providing bacteria carrying a gene that encodes β-lactamase; incubating the bacteria with a candidate compound under conditions that enable cell wall biosynthesis to form a reaction mixture;

assaying the reaction mixture for induction of β-lactamase to identify an inhibitor of cell wall biosynthesis; obtaining a cell extract containing enzymes, cofactors, and carrier molecules necessary for the particular step or steps; supplying a substrate for the step or steps; incubating the inhibitors with the cell extract and the substrate under conditions that enable the step or steps to proceed; and assaying the incubation mixture (e.g., by chromatography) for the substrate and the product normally produced in the step or steps. The production of an amount of product less than that normally produced in the step or steps relative to the amount of substrate indicates the presence of an inhibitor of the step or steps.

The cell extract can be a whole cell, a cell membrane preparation, or a cytoplasmic extract, for example. The substrate can be detectably labeled (e.g., with a fluorescent tag, an isotopic label, or biotin).

The particular step of cell wall biosynthesis referred to above can be the enolpyruvyl transfer step catalyzed by MurA or MurZ; the reduction of uridine diphosphate N-acetylenolpyruvylglucosamine catalyzed by MurB; the addition of L-alanine to uridine diphosphate-N-acetylmuramic acid catalyzed by MurC; the addition of D-glutamic acid to uridine diphosphate-N-acetylmuramic acid-L-alanine catalyzed by MurD; the addition of meso-diaminopimelate to uridine diphosphate-N-acetylmuramic acid-dipeptide catalyzed by MurE; the addition of D-alanyl-D-alanine to uridine diphosphate-N-acetylmuramic acid-tripeptide catalyzed by MurF; the racemization of L-alanine to D-alanine catalyzed by Ala racemase; the ligation of two molecules of D-alanine catalyzed by D-Ala:D-Ala ligase; the synthesis of lipid-linked N-acetylmuramic acid-pentapeptide catalyzed by MraY; the N-acetylglucosamine transfer step catalyzed by MurG; septum peptidoglycan synthesis catalyzed by the peptidoglycan transglycosylase-transpeptidase FtsI; or septum peptidoglycan synthesis catalyzed by FtsW.

An effective amount of a compound identified by these methods as an inhibitor of bacterial growth or as an inhibitor of particular steps in cell wall biosynthesis can be administered to an organism as a method of treating bacterial infection. An "effective amount" of a compound is an amount of the compound that, upon administration to an existing organism, reduces the spread of or completely eradicates a bacterial infection, or that prevents infection.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

The new methods represent a surprising discovery in that compounds that kill or inhibit the growth of bacteria can be identified at levels below their respective minimum inhibitory concentrations (MIC) by assaying for the induction of β-lactamase. Previous screens for bacteriocidal and bacteriostatic compounds looked for inhibition; the present methods are based on induction.

The new methods have numerous advantages. For example, the methods are used to detect induction of β-lactamase, rather than indirectly observing inhibition of β-lactamase by assaying for intact β-lactams or identifying an MIC by looking for absence of growth. As a result, the new methods allow detection of interruptions in steps of the cell wall biosynthesis process other than just those provoked by β-lactams.

Other advantages include efficiency, ease of use, good quantitation, sensitivity (e.g., effective drugs can be detected at concentrations below the MIC), reliability, reproducibility, selectivity, facility, versatility (e.g., the methods are adaptable from benchtop to high throughput screening methodology), and robustness (e.g., the screening methods can use natural product extracts which are very dirty).

The high sensitivity of the new methods can allow detection of certain compounds that are neither bacteriostatic nor bacteriocidal but nonetheless affect cell wall biosynthesis. Although such compounds might not themselves be effective drugs, they can be used to lead to novel drugs. For example, the compounds discovered by any of the new methods can serve as a basis for the design of structural analogs, some of which are likely to be more effective than the initially discovered compounds. The structural analogs can also be screened by the new methods.

Furthermore, the new methods allow screening for inhibitors of reactions, rather than inhibitors of enzymes. This is important for at least two reasons. First, some known inhibitors of cell wall biosynthesis (e.g., vancomycin) bind to the substrate of a reaction thereby rendering that substrate unavailable for reaction with an enzyme. The enzyme itself is not affected by the inhibitor; nonetheless the observed result is the same (i.e., the enzymatic reaction is ceased). Second, multiple steps in cell wall biosynthesis can be carried out by a single, multiple domain enzyme, while certain inhibitors can block the activity of just one of the domains. For example, two of the final transformations in cell wall biosynthesis are mediated by a single enzyme having two domains, only one of which is inactivated by β-lactam antibiotics.

Other features and advantages of the invention will be apparent from the following detailed description, and from the claims.

DETAILED DESCRIPTION

Figure 1:
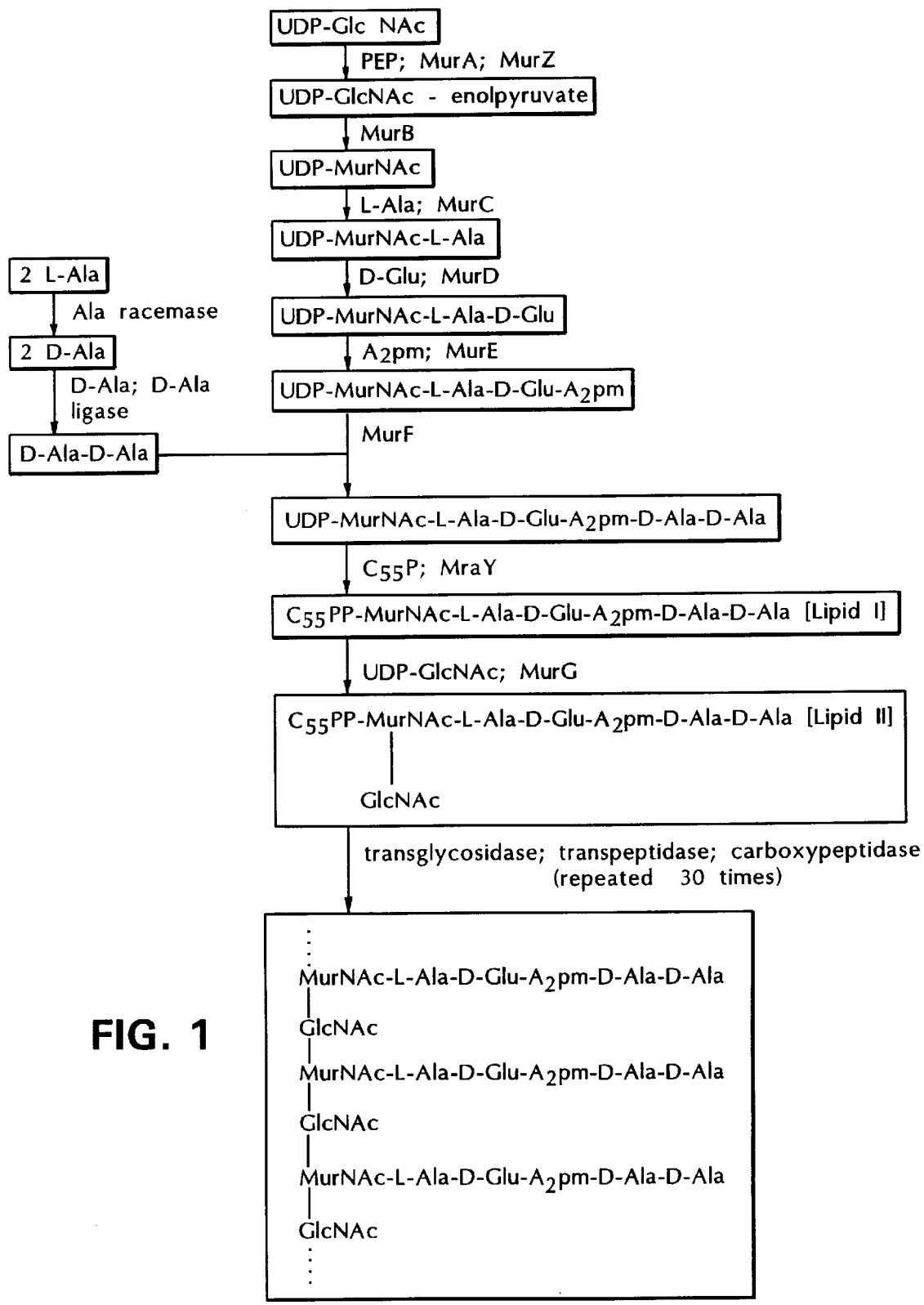
FIG. 1 is a flow chart of a generalized peptidoglycan biosynthetic pathway.

A screening method has been designed to detect compounds that kill or inhibit the growth of bacteria (e.g., for use in the treatment of bacterial infections in mammals or other organisms) by assaying for the induction of β-lactamase.

The new methods can be used, for example, for identifying inhibitors of cell wall biosynthesis. The screen can detect agents that inhibit the first committed step in cell wall biosynthesis, a phosphoenolpyruvyl (PEP) transferase reaction carried out by the MurA protein; the last step, transpeptidation carried out by penicillin binding proteins; or any other of the intermediate steps such as those carried out by MurB, MurC, MurD, MurE, MurF, Ala racemase, or Ddl, which are all known proteins involved in the cell wall biosynthetic pathway. The screen can also detect agents that inhibit other steps involved in or leading to cell wall biosynthesis that are not listed above, such as lipid carrier recycling steps.

The sensitivity of the screen has been tested using known antibiotics such as ramoplanin, a compound that inhibits the MurG reaction (i.e., conversion of Lipid I to Lipid II). The screen detected ramoplanin at a concentration significantly below the minimum inhibitory concentration (MIC). The specificity of the screen has also been tested, by screening against a molecular library of 1,840 compounds specially selected to bring to light any nonspecific detection events.

General Procedure

Practice of the new methods generally involves two stages: first, an induction screen, which indicates whether or not there is induction of β-lactamase, and second, a biochemical assay, which indicates whether or not there is inhibition of a particular step in the peptidoglycan biosynthesis. The latter stage is optional since simply identifying that a drug blocks cell wall biosynthesis is often sufficient to establish that the drug can be a useful antibacterial agent; nonetheless, assays are known for detecting inhibition of each step. Some representative, non-limiting examples of biochemical assays are included below for illustration.

Induction Screen

The first stage of the new antibiotic screening methods uses the induction of β-lactamase as a signal of antibiotic activity. The screen can be carried out in bacteria that carry an inducible gene encoding β-lactamase.

Bacteria carrying a gene that encodes β-lactamase, provided for use in the new methods, can be obtained from nature or from a laboratory, created by transformation of other bacteria, purchased, or otherwise acquired. The gene is not necessary native to the host bacterial strain; the host can be heterologous. The plasmid, cosmid, vector, or other nucleic acid molecule carrying the gene can, for example, be introduced into the bacteria using standard protocols such as calcium chloride transformation (see, e.g., Ausubel et al., *Current Protocols in Molecular Biology*, John Wiley & Sons, 1989).

β-Lactamase is produced by numerous species. For example, the ampC gene of *Citrobacter freundii* encodes β-lactamase. Any inducible β-lactamase gene is suitable for use with the new methods. Most species of Citrobacter, Enterobacter, Serratia, and Pseudomonas, as well as indole-positive Proteus species have a β-lactam-inducible enzyme (Lindberg et al., *Proc. Natl. Acad. Sci.*, 82:4620–4624, 1985).

The ampC gene from Citrobacter freundii encodes β-lactamase, which is expressed at a high level when cells are exposed to certain β-lactam antibiotics, such as cefoxitin. The ampR gene encodes a repressor molecule that binds to DNA within the regulatory region of the ampC gene, shutting down its expression. A breakdown product of cell wall degradation, anhydromuramyl-tripeptide interacts with AmpR, resulting in induction of β-lactamase (Park, *Molecular Microbiology*, 17:421–426, 1995). AmpR is thus a transcriptional regulator of ampC, encoding β-lactamase.

Figure 2:
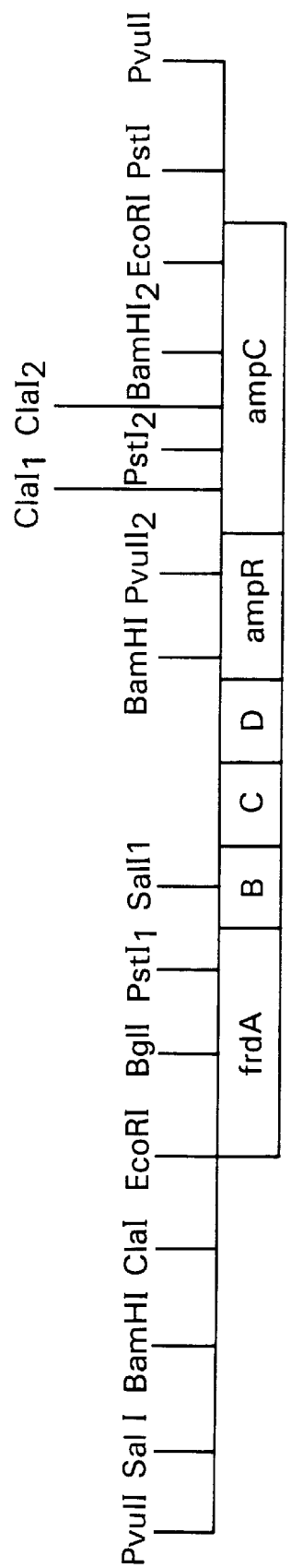
FIG. 2 is a map of the pNU305 plasmid.

The ampC and ampR genes have been cloned into a plasmid, pNU305, with which several strains of *E. coli* were transformed (Lindberg et al., *Proc. Natl. Acad. Sci.*, 82:4620–4624, 1985). A map of the plasmid is shown in FIG. 2.

Other β-lactamase genes (e.g., from Enterobacter, Serratia, or Pseudomonas) can also be cloned into a plasmid, cosmid, vector, or other nucleic acid molecule using standard molecular biological techniques. For example, a pair of polymerase chain reaction (PCR) primers (e.g., having 20, 30, 40, or more nucleotides) could be synthesized (e.g., on an automated oligonucleotide synthesizer) that would each complement an end of the β-lactamase gene. These two primers can each contain a restriction site. The gene can then be amplified using PCR to generate a product having the gene flanked by the restriction sites introduced by the PCR primers. An appropriate cloning vector and the PCR product can be digested with a suitable restriction enzyme, mixed, and ligated to incorporate the gene into the vector (see, e.g., Ausubel et al., supra; Sambrook, et al., *Molecular Cloning*, Cold Spring Harbor Laboratory Press, 1989).

The plasmid pNU305 was introduced into host *E. coli* strains carrying an envA-mutation. These strains retain partially regulated expression of β-lactamase, but also have the additional advantage of increased permeability to larger molecules (e.g., antibacterial agents normally having activity exclusively against gram-positive bacteria), making the strain hypersensitive and thus suitable for drug screening.

Examples of suitable bacteria for use as the host in the new screening methods include, but are not limited to, *Streptococcus albus, Bacillus sphaericus, Bacillus subtilis, Bacillus licheniformis, Streptococcus pneumoniae, Staphylococcus simulans, Staphylococcus aureus, Lactobacillus lactis, Lactobacillus delbrueckii*, Chalaropsis sp., *Streptococcus globosporus, Clostridium acetobutylicum, Enterococcus hirae, Streptococcus faecalis, Escherichia coli, Arthrobacter crystallopoietes, Bacillus cereus, Bacillus stearothermophilus, Bacillus thuringiensis, Brucella abortus, Clostridium botulinum, Clostridium welchii, Lactobacillus acidophilus, Listeria monocytogenes, Micrococcus luteus, Mycobacterium smegmatis*, Myxobacter sp., *Neisseria gonorrhoeae, Proteus vulgaris, Pseudomonas aeruginosa, Salmonella typhimurium, Streptococcus hygrocopicus, Streptococcus pyogenes, Pseudomonas fluorescens, Streptomyces griseofuscus, Enterococcus faecalis, Streptomyces roseosporus, Actinomyces utahensis, Streptomyces fradiae, Staphylococcus epidermidis, Clostridium difficile, Bacillus megaterium, Klebsiella aerogenes, Pseudomonas cocovenenans, Streptomyces cattleya, Empedobacter lactamgenus*, and *Aspergillus candidus*.

The bacteria are contacted (e.g., incubated) with a candidate compound, which can be any compound not previously known to inhibit bacterial growth. The candidate compound can be, for example, a single compound or a member of a library of potential inhibitors.

Incubation times vary with species and incubation temperature (e.g., 1 hour, 12 hours, 1 day, 2 days, a week, or longer). Suitable conditions that normally allow cell wall biosynthesis can include aerobic or anaerobic atmospheres at room temperature or lower, 30° C., 37° C., or higher, depending on the species of bacteria.

A library of potential inhibitors can be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of potential inhibitors can include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library can contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) can also be used with the new methods.

In addition to libraries of potential inhibitors, special libraries called diversity files can be used to assess the specificity, reliability, or reproducibility of the new methods. Diversity files contain a large number of compounds (e.g., 1000 or more small molecules) representative of many classes of compounds that could potentially result in non-specific detection in an assay. Diversity files are commercially available or can also be assembled from individual compounds commercially available from the vendors listed above.

Assays are then carried out to determine the level of β-lactamase induction and thus the effectiveness of the inhibitors. In general, the higher the level of induction, the higher the level of effectiveness of a given inhibitor candidate. Assays for β-lactamase can be carried out, for example, by spectrophotometry (e.g., by measuring the optical absorbance of the reaction mixture, for instance, at 490 nm), by producing antibodies that specifically bind to β-lactamase, or by probing for β-lactamase mRNA (e.g., using a labeled probe; the label can be, for instance, fluorescent, radioactive, or biotinylated). Spectroscopic methods (e.g., high performance liquid chromatography, HPLC) can also be used, as can electrophoresis (agarose gel, polyacrylamide gel electrophoresis, etc.) or affinity chromatography. In another alternative, labeled substrates can be used to assay for β-lactamase activity.

Antibodies that specifically recognize one or more epitopes of β-lactamase, or epitopes of conserved variants of β-lactamase, or peptide fragments of β-lactamase can be used to assay for β-lactamase induction. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

For the production of antibodies, various host animals may be immunized by injection with the β-lactamase, a β-lactamase peptide, truncated β-lactamase polypeptides, functional equivalents of the β-lactamase or mutants of the β-lactamase. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (*Nature*, 256:495–497, 1975; and U.S. Pat. No. 4,376,110), the human B-cell hybridoma technique (Kosbor et al., *Immunology Today*, 4:72, 1983; Cole et al., *Proc. Natl. Acad. Sci. USA*, 80:2026–2030, 1983), and the EBV-hybridoma technique (Cole et al., *Monoclonal Antibodies And Cancer Therapy*, Alan R. Liss, Inc., pp. 77–96, 1985). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Alternatively, techniques described for the production of single chain antibodies (U.S. Pat. No. 4,946,778; Bird, *Science*, 242:423–426, 1988; Huston et al., *Proc. Natl. Acad. Sci. USA*, 85:5879–5883, 1988; and Ward et al., *Nature*, 334:544–546, 1989) can be adapted to produce single chain antibodies against β-lactamase. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., *Science*, 246:1275–1281, 1989) to allow rapid and easy identification of monoclonal Fab fragments with the desired specificity.

Antibodies to β-lactamase can, in turn, be utilized to generate anti-idiotype antibodies that "mimic" the β-lactamase, using techniques well known to those skilled in the art. (See, e.g., Greenspan et al., *FASEB J.*, 7(5):437–444, 1993; and Nissinoff, *J. Immunol.*, 147(8):2429–2438, 1991).

Yet another method for assaying for β-lactamase induction uses a reporter gene (e.g., lacZ, luc), the product of which is detectable by established methods. For example, lacZ encodes β-galactosidase, which is simple to detect biochemically. The luc gene encodes luciferase, a bioluminescent protein that can be detected with a low-light camera. The reporter gene can be inserted into the same open reading frame (ORF) as the β-lactamase gene in the plasmid, cosmid, vector, bacterial chromosome or other nucleic acid molecule carrying the β-lactamase gene. The reporter gene is preferably under the control of the same inducer, promoter, or regulator, or combination thereof, that controls the expression of the β-lactamase gene. Other variants of reporter genes are also within the scope of the invention, including other gene fusion products and other genetically encoded fluorescent tags.

The new methods can be carried out in nearly any reaction vessel or receptacle. Examples of suitable receptacles include 96-well plates, 384-well plates, test tubes, centrifuge tubes, and microcentrifuge tubes. The methods can also be carried out on surfaces such as on metal, glass, or polymeric chips, membrane surfaces, the surface of a matrix-assisted laser-desorption ionization mass spectrometry (MALDI-MS) plate, on a resin, and on a glass, metal, ceramic, paper, or polymer surface.

Biochemical Assay

The second stage of the new methods is a simulation of a particular step or steps in the cell wall biosynthesis pathway in a biochemical assay. This assay is optional. For example, if the goal is simply to screen for antibacterial activity, it is not necessary to carry out the biochemical assay. If it is desirable to identify whether or not a particular step or steps are inhibited, then the biochemical assay can be carried out.

FIG. 1 shows a general scheme of peptidoglycan synthesis. MurA and MurZ catalyze the first reaction, the transfer of enolpyruvate from phosphoenolpyruvate (PEP) to uridine diphosphate N-acetylglucosamine (UDP-GlcNAc) to form UDP-GlcNAc-enolpyruvate. The GlcNAc-enolpyruvate is then replaced with N-acetylmuramic acid (MurNAc) by MurB to generate UDP-MurNAc. L-Ala, D-Glu, and meso-diaminopimelic acid ($A_2$pm) are then added to form a UDP-MurNAc-tripeptide. In some bacteria, L-Lys is added in place of $A_2$pm. The additions of L-Ala, D-Glu, and $A_2$pm are catalyzed by MurC, MurD, and MurE, respectively.

In a separate reaction series, L-Ala is racemized to D-Ala by Ala racemase. Two molecules of D-Ala are linked together to form D-Ala-D-Ala by D-Ala:D-Ala ligase (Ddl), an ATP-dependent enzyme.

D-Ala-D-Ala adding enzyme (MurF), also an ATP-dependent enzyme, catalyzes the coupling of D-Ala-D-Ala to the UDP-MurNAc-tripeptide to form a UDP-MurNAc-pentapeptide.

Translocase MraY catalyzes the nucleophilic attack of undecaprenyl phosphate ($C_{55}P$) with the pentapeptide to form MurNAc(pentapeptide)-pyrophosphorylundecaprenol, also called Lipid I. MurG catalyzes the addition of a molecule of UDP-GlcNAc to Lipid I to form GlcNAc-MurNAc-(pentapeptide)-pyrophosphorylundecaprenol, also called Lipid II.

In the final stages of peptidoglycan biosynthesis, Lipid II is polymerized by repeated coupling reactions catalyzed by a transglycosidase, a transpeptidase, and a carboxypeptidase. The transglycosidase and transpeptidase activities can be present in a single, multidomain enzyme such as the peptidoglycan transglycosylase-transpeptidase FtsI. The penicillin binding proteins (e.g., PBP1, PBP2, or PBP3) are multiple domain proteins that have carboxypeptidase activity. For example, FtsW, the PBP3-associated protein, can carry out the carboxypeptidase step. An average of about thirty Lipid II subunits are assembled in this manner to form the peptidoglycan unit ("Bacterial Cell Wall," Ghuysen and Hackenbeck, Eds., Chapters 3 and 4, Elsevier, Amsterdam, 1994).

A cell extract is obtained that contains all of the components (i.e., enzymes, cofactors, carrier molecules, and buffers) normally necessary for the particular step or steps for which inhibition is to be assayed to proceed. The components should be sufficient for carrying out the transformation of a substrate for the step or steps to the corresponding product.

Cell extracts containing enzymes, cofactors, and carrier molecules can be cytoplasmic, cytosolic, or membrane preparations, whole cells, naturally-occurring or synthetic mixtures made up of natural or unnatural components, or both.

The carrier molecules included in the cell extracts can include numerous components, such as molecular transport machinery and membranes. The substrate for the reaction can be contained within the cell extract initially or can be added in solution, as a dry additive, or can be generated in situ (e.g., as the product of another reaction).

The substrate for the particular step or steps is then supplied (e.g., in a solution, in a suspension or dispersion, as a solid, as a liquid, or as the product of a prior step). The substrate can be detectably labeled, for example, with a tag, a radiolabel, a fluorescent label, a magnetic label, or as a biotinylated derivative.

After incubation of the cell extract/substrate mixture under conditions that normally allow the particular step or steps to proceed, the mixture is assayed to determine whether or not the substrate remains and whether or not the corresponding product or products have been formed.

The duration of incubation varies with the particular step or steps being carried out and also with incubation temperature (e.g., 1 hour, 12 hours, 1 day, 2 days, a week, or longer). Suitable conditions that normally allow the step or steps to proceed can include aerobic or anaerobic atmospheres at room temperature or lower, 30° C., 37° C., or higher, depending on the species of bacteria.

Suitable methods for assaying for the remaining substrates or for the products, or both, include fluorescence microscopy, infrared spectroscopy, Raman spectroscopy, fluorescence polarimetry, mass spectroscopy (e.g., using matrix-assisted laser-desorption, electrospray, or other ionization techniques, or time-of-flight mass spectroscopy), thin layer chromatography (TLC), high pressure liquid chromatography (HPLC), capillary electrophoresis (CE), gel electrophoresis, gas chromatography (GC), reverse phase chromatography (RPC), size exclusion chromatography (SEC), FPLC, or flash chromatography (on alumina, silica, etc.).

To screen for inhibition of the step catalyzed by MurB, for example, a reaction mixture can be prepared, containing a salt of phosphoenolpyruvate (e.g., a cyclohexylammonium salt), reduced nicotinamide adenine dinucleotide phosphate (NADPH), $^{14}$C-UDP-GlcNAc, the drug to be screened, and a cell extract (Miyakawa et al., *J. Bacteriology*, 112(2):950–958, 1972). A buffer solution such as Tris-HCl pH 7.8 with salts (KCl, $MgCl_2$, etc.) can also be added. After incubating the reaction mixture, the reaction can be quenched (e.g., with acid) and the mixture subjected to chromatography (e.g., HPLC, FPLC, TLC, flash chromatography, or paper chromatography). Paper chromatography with 5:3 (v:v) isobutyric acid/1 M ammonia, for example, allows separation of UDP-GlcNAc ($R_f$ 0.30) and UDP-MurNAc ($R_f$ 0.35). By comparing the ratio of these components, it can be determined whether or not MurB has been inhibited by the drug. The presence of the latter product indicates that MurB is functional, i.e., has not been inhibited.

Similarly, to screen for inhibition of the step catalyzed by MurC, a reaction mixture can be prepared containing adenosine triphosphate (ATP), D-cycloserine, UDP-MurNAc, $^{14}$C-L-alanine, the drug to be screened, and a cell extract. A buffer solution such as Tris-HCl pH 8.0 with salts ($MnCl_2$, etc.) can also be added (ibid.). After incubating the reaction mixture, the reaction can be quenched (e.g., by heating) and the mixture subjected to chromatography (e.g., HPLC, FPLC, TLC, flash chromatography, paper chromatography, etc.). Paper chromatography with 5:3 (v:v) isobutyric acid/1 M ammonia, for example, allows isolation of UDP-MurNAc-L-Ala. The incorporated radioactivity can be quantified and compared to a control sample (i.e., without the drug) to determine whether or not MurC has been inhibited by the drug. The less UDP-MurNAc-L-Ala that is detected, the greater the inhibition.

By substituting $^{14}$C-D-Glu and UDP-MurNAc-L-Ala or $^{14}$C-$A_2$pm and UDP-MurNAc-L-Ala-D-Glu, respectively, for $^{14}$C-L-Ala and UDP-MurNAc, the activities of MurD and MurE can be similarly probed (ibid.).

To screen for inhibition of the steps catalyzed by ddl or MurF, a reaction mixture can be prepared containing adenosine triphosphate (ATP), UDP-MurNAc-L-Ala-D-Glu-$A_2$pm, $^{14}$C-L-alanine, $^{14}$C-DL-alanine, or $^{14}$C-D-Ala-$^{14}$C-D-Ala, the drug to be screened, and a cell extract (ibid.). A buffer solution such as Tris-HCl pH 7.8 with salts ($MnCl_2$, etc.) can also be added. After incubating the reaction mixture, the reaction can be quenched (e.g., by heating) and the mixture subjected to chromatography (e.g., HPLC, FPLC, TLC, flash chromatography, paper chromatography, etc.). Paper chromatography with 5:3 (v:v) isobutyric acid/1 M ammonia, for example, allows isolation of UDP-MurNAc-pentapeptide or D-Ala-D-Ala. The incorporated radioactivity can be quantified and compared with control samples to determine whether or not Ddl or MurF has been inhibited by the drug. If UDP-MurNAc-pentapeptide is decreased relative to the control sample, MurF or Ddl is likely inhibited. To distinguish between these, the level of D-Ala-D-Ala is assayed; a low concentration of D-Ala-D-Ala in combination with a low concentration of the UDP-MurNAc-pentapeptide is indicative of inhibition of Ddl, while build-up of D-Ala-D-Ala suggests that MurF is inhibited.

Finally, these methods can be used to identify inhibition of cell membrane-bound peptidoglycan synthetase, peptidoglycan transpeptidase, or D-Alanine carboxypeptidase by using UDP-MurNAc-L-Ala-D-Glu-A$_2$pm-$^{14}$C-D-Ala-$^{14}$C-D-Ala as a substrate (ibid.). The product levels are assayed, as described for the other steps, and compared with control samples to deduce the identity of the inhibited step.

Uses of Inhibitory Compounds

Compounds identified via the new methods as inhibitors of bacterial growth using the new methods can be used to treat bacterial infections in an organism (e.g., a mammal such as a human). To this end, an effective amount of the compound can be administered to the organism.

The effective amount of a compound used to practice the present invention varies depending upon the extent, nature (e.g., bacterial species, affected organ), and severity of the infection to be treated, the manner of administration, the age, body weight, and other conditions of the organism to be treated, and ultimately will be decided by the attending physician, veterinarian, or experimenter. The effective amount of a compound to be administered can depend on body surface area, weight, and overall condition of the organism. The interrelationship of dosages for animals and humans (based on milligrams per meter squared of body surface) is described by Freireich, E. J., et al., *Cancer Chemother. Rep.*, 50 (4), 219 (1966). Body surface area may be approximately determined from patient height and weight. See, e.g., Scientific Tables, Geigy Pharmaceuticals, Ardley, N.Y., pages 537–538, 1970. An effective amount of the compound for practicing the present invention can range from about 5 µg/kg to about 500 mg/kg, e.g., from about 500 µg/kg to about 250 mg/kg or from about 1 to about 150 mg/kg. Effective doses will also vary, as recognized by those skilled in the art, dependant on route of administration, excipient usage, and the possibility of co-usage with other therapeutic treatments.

The formulations may conveniently be presented in unit dosage form and may be prepared by any of the methods well known in the art of pharmacy. All methods include the step of bringing the active ingredient or ingredients into association with a suitable carrier which constitutes one or more accessory ingredients, unless the compound can be administered in a pure form. In general, the formulations for tablets or powders are prepared by uniformly and intimately blending the active ingredient with finely divided solid carriers, and then, if necessary as in the case of tablets, forming the product into the desired shape and size.

The compounds described here can be administered by any route appropriate to the infection being treated. They can be injected into the bloodstream of the subject being treated, applied topically, or administered orally, subcutaneously, or intraperitoneally. However, it will be readily appreciated by those skilled in the art that the route, such as intravenous, subcutaneous, intramuscular, intraperitoneal, nasal, oral, etc., will vary with the condition being treated and the activity of the compound being used. The invention will be further described in the following examples, which do not limit the scope of the invention described in the claims.

EXAMPLES

Example 1

β-Lactamase Induction Screen

Screening Strain: *E. coli* strain D22 carrying plasmid pNU305 which contains the ampC and ampR genes from *Citrobacter freundii*, the envA-allele, a colEI origin of replication, and a tetracycline resistance determinant was grown in Luria Broth (LB; 5 g yeast extract, 10 g tryptone, and 10 g sodium chloride per liter of purified water) supplemented with E salts (400 µl E salts per 100 ml LB; the E salts contained 10 g magnesium sulfate heptahydrate, 100 g citric acid monohydrate, 500 g anhydrous dibasic potassium phosphate, and 175 g of monosodium monoammonium phosphate tetrahydrate per liter of purified water).

Agar plates were prepared with the LB/E salts and 10 µg/ml tetracycline.

Reaction Buffer: Nitrocefin was dissolved in dimethylsulfoxide (DMSO) to a concentration of 25 mg/ml and stored in 1 ml aliquots at −80° C. To prepare a reaction buffer, one of the nitrocefin/DMSO aliquots was added to 50 ml Z buffer with detergents (16.1 g dibasic sodium phosphate heptahydrate, 5.5 g monobasic sodium phosphate monohydrate, 0.75 g potassium chloride, 246 mg magnesium sulfate heptahydrate, 200 mg CTAB, and 100 mg sodium deoxycholate per liter, with the pH adjusted to 7.0) and the mixture was vortexed vigorously. The resulting suspension was filtered through Q5 filter paper (Fisher, Cat. No. 09-790-2e) to remove insoluble material. The filtered reaction buffer was stored at −80° C. until it was needed.

Growth Regimen: A single colony of the *E. coli* (i.e., a starter colony) was streaked onto an LB plate (with tetracycline) and incubated overnight at 37° C. Cells from the starter colony were then used to inoculate multiple colonies in LB (without tetracycline) to give a cell density no higher than 0.05 OD at 650 nm. The cells were grown at 37° C. under aerating conditions (i.e., shaken at 200 rpm in Erlenmeyer flasks having a volume of at least 10 times that of the culture.

Screening: When the cells had grown to a cell density of 0.25 to 0.8 OD at 650 nm, the culture was diluted to 0.25 OD. 80 µl of the diluted culture was added to each well of a microtiter plate containing 20 µl samples from a simulated natural product library, using an automated liquid dispensing robot from Titrtek (Huntsville, Ala.).

The simulated natural product library contained a two-fold dilution series of known antibiotics cefoxitin, cycloserine, fosfomycin, moenomycin, ramoplanin, vancomycin, bacitracin, ciprofloxacin, erythromycin, and rifampicin. All but the last three of these compounds are known to inhibit cell wall biosynthesis. Ciprofloxacin inhibits DNA replication, rifamycin inhibits RNA synthesis, and erythromycin affects protein synthesis. Several surfactants were also represented in the library, including monensin, nisin, polymyxin B nonapeptide, polymyxin B sulfate, sodium dodecyl sulfate, and Triton X-100.

A positive control compound (25 µg/ml fosfomycin) was added to some of the wells and other wells were left untreated, as negative control samples. The samples were incubated on the plate for one hour at 37° C. without shaking.

Assay: 10 µl aliquots were transferred from each well to a second microtiter plate, using a Quadra 96 Model 320 robot (TomTec, Hamden, Conn.). 90 µl of the reaction buffer prepared above was added to each well using a automated liquid dispensing robot (Titrtek, Huntsville, Ala.). The OD of the samples was immediately read at 490 nm in a plate reader (Biorad, Model 3550) to obtain zero point β-lactamase levels. The OD was measured again after incubating the plates at room temperature for 90 minutes (room temperature near 30° C.) or 120 minutes (room temperature below 30° C.).

Data Analysis: An induction value, I, was determined for each sample according to the following formula: I=(OD of sample−median OD)/(OD of induced cells−median OD); where the median OD was determined for each plate and the OD of induced cells was defined as the average of the readings from the control wells exposed to the 25 μg/ml fosfomycin. Inactive samples were defined as those having I=0. Fully induced samples had I=1. Any sample having I≧0.2 was considered to be positive. Since the assay is calorimetric, the zero-point levels were subtracted from the OD readings.

To determine the minimum inhibitory concentration (MIC) and the limit of detection of ramoplanin in envA-cells containing the pNU305 plasmid, the cells were diluted to a concentration of $5 \times 10^5$/ml and incubated at 37° C. for 18 hours in a 96-well plate containing a series of 13 two-fold dilutions of ramoplanin (i.e., from 50.0 μg/ml down to 12.2 ng/ml).

The optical density (OD) of each reaction mixture was measured at 655 nm. The lowest concentration of ramoplanin for which the OD reading was zero was taken to be the MIC. The experiment was repeated several times and the MIC values were averaged to give a value of about 20 μg/ml of ramoplanin.

Figure 3A:
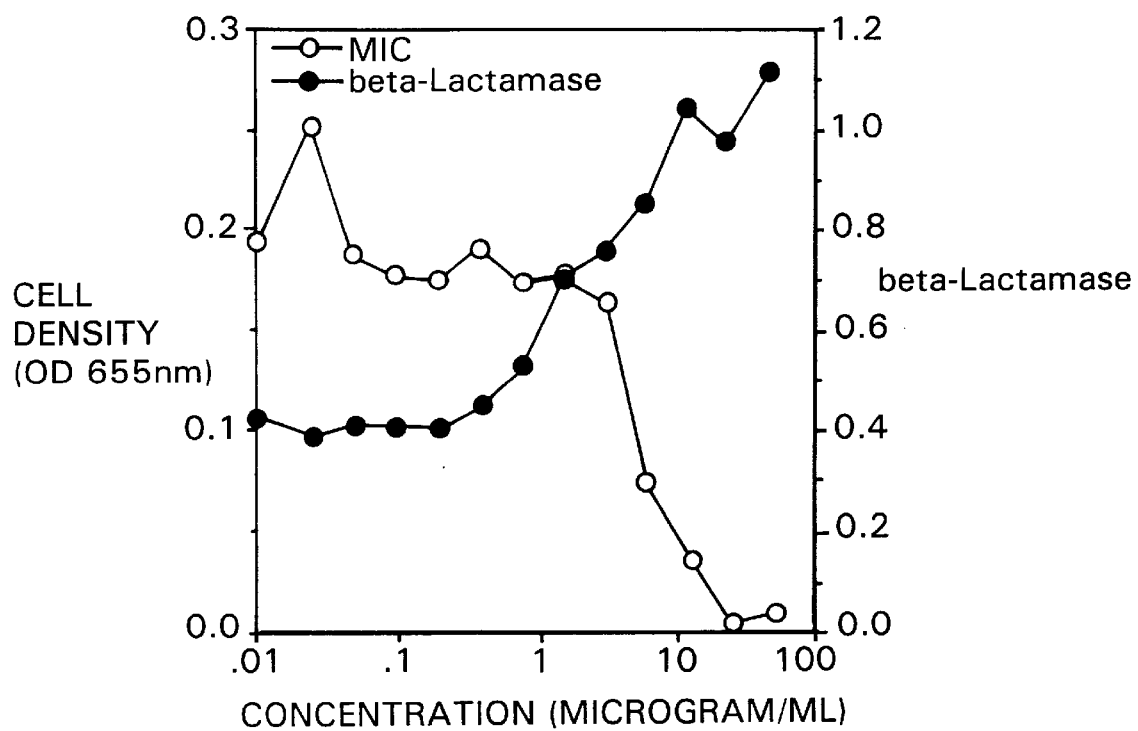
FIGS. 3A and 3B are graphs that simultaneously indicate both cell density and β-lactamase levels, plotted against the concentration of ramoplanin.
Figure 3B:
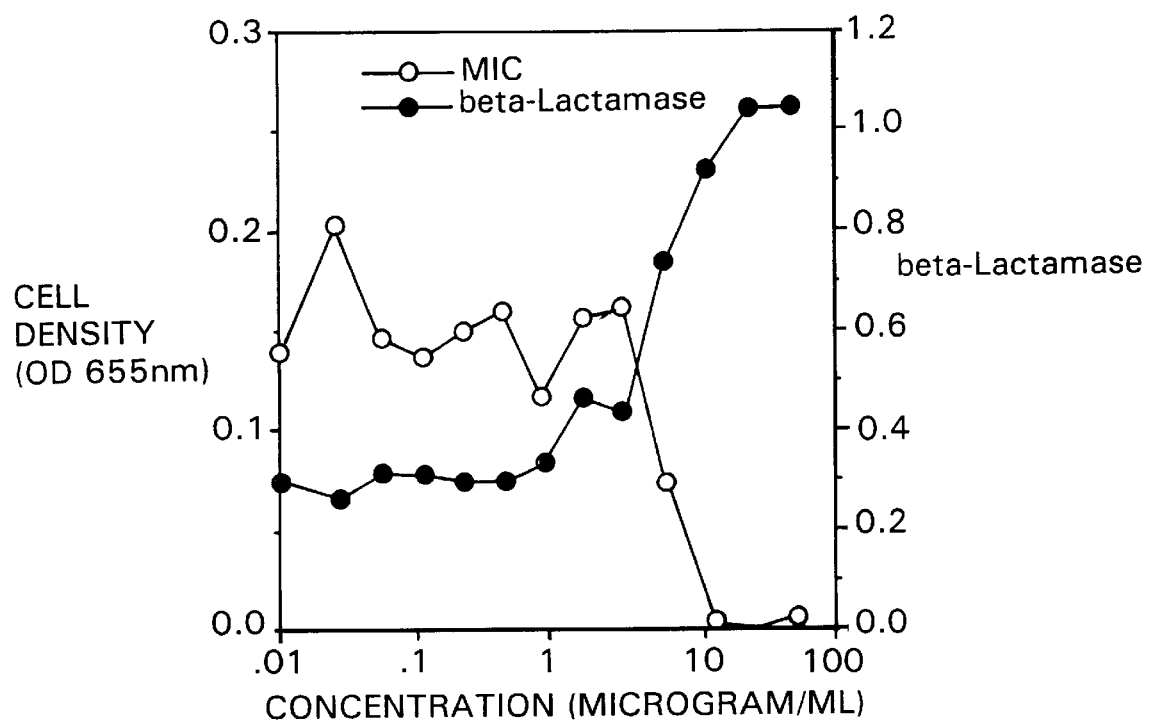

The same mixtures were also screened for increased β-lactamase using the new methods. The β-lactamase produced was plotted against the logarithm of ramoplanin concentration. FIGS. 3A and 3B show two examples of such plots. As shown by the leftmost 6 and 7 solid black circles in FIGS. 3A and 3B, respectively, these plots show no effect of low concentrations of added ramoplanin on β-lactamase induction, up to a ramoplanin concentration of about 0.8 to 1.6 μg/ml. At this level, the β-lactamase induction level began to increase. This level was taken to be the limit of detection of the screening procedure. Over a series of trials, the average onset of increased induction was found to be about 1.8 μg/ml.

Thus, the envA-strain was able to detect the activity of ramoplanin at a concentration about 11 (i.e., 20/1.8) times less than the minimum inhibitory concentration.

The MIC and the limit of detection of β-lactamase induction for the other members of the library are given in Table 1.

Example 2

Diversity File

A diversity file including twenty 96-well plates each with 92 compounds and 4 empty wells (i.e., two for positive control samples, two for negative control samples) was obtained. The diversity file contained a library of small molecules (i.e., molecular weight ranging from 10 to 1000), with 1840 compounds in total, representative of many classes of compounds that could potentially result in non-specific detection. The file allows determination of whether or not the screening method consistently identifies positive hits.

The cells were prepared in the same manner as described in Example 1, except that they were diluted to an optical density of 0.083, and 100 μl of the resulting cell suspension was then added to wells, each preloaded with 10 μl (1 μg) of a file compound in Hepes solution. The final concentration of compound was therefore 10 μg/ml in

TABLE 1

| Compound | [Induction] (μg/ml) | MIC (μg/ml) |
|---|---|---|
| Cefoxitin | 2.5 | 7 |
| Cycloserine | 20 | 12.5 |
| Fosfomycin | 0.7 | 0.7 |
| Moenomycin | 1 | 2 |
| Ramoplanin | 1.8 | 20 |
| Vancomycin | 4 | 10 |
| Bacitracin | 1.6 | 12.5 |
| Ciprofloxacin | none | 0.01 |
| Erythromycin | none | 0.8 |
| Rifampicin | none | 0.06 |
| Monensin | none | >100 |
| Nisin | none | >100 |
| Polymyxin B nonapeptide | 6.3 | >100 |
| Polymyxin B sulfate | 0.2 | 0.4 |
| Sodium dodecyl sulfate | 4 | 2 |
| Triton X-100 | 100 | 500 | each screening well, and 25 μg/ml fosfomycin in the positive control wells. Cells alone were added to the negative control wells.

Following the 90 to 120 minute incubation, β-lactamase was measured calorimetrically as described in Example 1.

As mentioned above, each of the diversity file plates had 4 empty control wells (i.e., E-12 to H-12). On some of the plates, ramoplanin was added at 20 μg/ml and 10 μg/ml in wells E12 and F12, respectively; as above, wells G12 and H12 were loaded only with cells. Other cell wall active drugs such as fosfomycin or cefoxitin can be substituted for ramoplanin.

The background level of β-lactamase produced by untreated cells was found to approach 50% of the level produced by drug-induced cells. The background level is highly variable over extended time periods, but is stable for a given batch of plates (at least 10 screening plates) assayed within a short time period.

About 0.3% of the diversity file samples were "strong" hits, meaning that they exhibited induction comparable to that observed when cells are exposed to 10 μg/ml ramoplanin. If a hit is more broadly defined as any sample that induces significantly above the background of β-lactamase produced by untreated cells, the hit rate goes up to about 1.0%. These hit rates are in a range that is acceptable for a useful and effective primary screen.

The 1.0% of samples that induced above background were detected by selection of statistically significant deviations above the untreated controls and the majority of wells that lacked activity. The "strong" hits were easily detected by eye, and were confirmed by measurement with instrumentation.

Example 3

Biochemical Assay for murG, mraY, and Transglycosylation Activities

An in vitro murg biochemical assay that utilizes E. coli membranes to catalyze the late steps in cell wall biosynthesis was used (Mengin-Lecreaulx et al., J. Bacteriology, 173:4625–4636, 1991) to confirm and elaborate on the induction screen of Example 1. As described above, cell wall activities associated with the membranes include the MraY protein (phospho-N-acetylmuramic acid-pentapeptide translocase), which transfers the MurNAc-pentapeptide to undecaprenyl phosphate to form Lipid I; the MurG gene product (N-acetylglucosamine transferase), which transfers N-acetylglucosamine to Lipid I, forming Lipid II; and enzymes that effect polymerization (i.e., transglycosylation and transpeptidation).

Two thin layer chromatography (TLC) assay formats (TLC Format #1 and TLC Format #2) were used to differentiate MraY, MurG, and transglycosylase inhibitors.

TLC Format #1 was used to monitor formation of Lipid II and peptidoglycan in reactions containing $E.\ coli$ membranes, UDP-MurNAc-pentapeptide, and $^{14}$C-labeled UDP-GlcNAc. The expected labeled reaction products (i.e., Lipid II and peptidoglycan) were separated by silica gel thin layer chromatography and detected by fluorography.

To prepare samples for TLC Format #1, 7.5 μl of a 25 μg/ml solution of the compound to be assayed was added to 3.5 μl distilled water in each well of a 96-well plate. 11.5 μl of a membrane mixture was added to each well. The membrane mixture contained 500 μl of 10 mg/ml $E.\ coli$ K802 membrane (including all the enzymes necessary for carrying out the late steps in cell wall synthesis, i.e., MurG, MraY, and transglycosylation and transpeptidation enzymes), 350 μl distilled water, and 300 μl 10× buffer; the 10× buffer contained 450 μl of a solution of 0.5 M Tris-HCl pH 8.0, 0.1 magnesium chloride, and 0.2 M potassium chloride in distilled water, added to 1 μl β-mercaptoethanol and 50 μl of 55 mg/ml ATP in distilled water.

After ten minutes, 6 μl of 0.25 mM UDP-MurNAc-pentapeptide was added to each well. After an additional 10 minutes, 5 μl of 2 μM $^{14}$C-labeled UDP-GlcNAc was added to each well (i.e., 0.5 nCi/well). The wells were then covered with plastic tape and the samples were incubated for 30 minutes. The reactions were quenched by boiling the plate for one minute in water.

2 μl of each sample were spotted onto silica-coated TLC plates with a Biohit Proline 8-channel pipettor (Biohit, Helsinki, Finland). After the samples had dried, the plates were lowered into a TLC tank containing 5:3 isobutyric acid:1 M ammonium hydroxide. The solvent was allowed to run up the plates for about 2 hours. The plates were dried, washed with acetone, and autoradiographic pictures were made. On the autoradiograph, it was observed that the peptidoglycan remained near the origin ($R_f$ 0), UDP[$^3$H] GlcNAc migrated to $R_f$ 0.3, and Lipid II migrated to $R_f$ 0.6.

Compounds that inhibited production of both Lipid II and peptidoglycan were concluded to be either MraY or MurG inhibitors. Those that reduced only peptidoglycan formation were concluded to be transglycosylase inhibitors.

TLC Format #2 was used to distinguish between inhibitors of MraY and MurG. Reactions were conducted as for TLC Format #1, with the exception that only the membranes and $^{14}$C-labeled MurNAc pentapeptide were added. No UDP-GlcNAc was used.

To prepare samples for TLC Format #2, 7.5 μl of a 25 μg/ml solution of the compound to be assayed was added to 13.5 μl distilled water in each well of a 96-well plate. 21.5 μl of a membrane mixture (500 μl of 10 mg/ml $E.\ coli$ K802 membrane, 1350 μl distilled water, and 300 μl 10× buffer; the 10× buffer contained 450 μl of a solution of 0.5 M Tris-HCl pH 8.0, 0.1 magnesium chloride, and 0.2 M potassium chloride in distilled water, added to 1 μl β-mercaptoethanol and 50 μl of 55 mg/ml ATP in distilled water) was added to each well. After ten minutes, 1 μl of UDP-MurNAc-$^{14}$C-DAP-pentapeptide (8000 cpm/μl) was added to each well. The wells were then covered with strip caps and the samples were incubated for 30 minutes. The reactions were quenched by boiling the plate for one minute in water.

2 μl of each sample were spotted onto silica-coated TLC plates with a BIOHIT™ 8-channel pipettor. After the samples had dried, the plates were lowered into a TLC tank containing 5:3 isobutyric acid:1 M ammonium hydroxide. The solvent was allowed to run up the plates for about 2 hours. The plates were dried, washed with acetone, and autoradiographic pictures were made. On the autoradiograph, it was observed that the UDP-MurNAc-$^{14}$C-DAP-pentapeptide remained near the origin, while Lipid I/Lipid II migrated to $R_f$ 0.6.

If the radiolabeled Lipid I/Lipid II appeared, it was concluded that MraY was operative and therefore MurG was not. Failure to produce any radiolabeled product led to the conclusion that MraY was shut down.

For each of the TLC Formats, the autoradiographs were scanned into a computer and analyzed to determine percentage inhibition for each sample.

Example 4

MurA Biochemical Assay

A spectrophotometric assay for inhibitors of UDP-GlcNAc enolpyruvyltransferase (MurA/MurZ) was used to confirm and elaborate on the results of the induction screen of Example 1.

Enzyme Isolation and Purification: MurA was isolated and purified according to the following procedure. A specimen of Myco strain 342 D-1-74, an overproducer of MurA, was streaked onto an LB plate (with 100 μg/ml ampicillin) and incubated overnight at 37° C. The following day, a single colony from the plate was used to inoculate 20 ml of LB (with 100 μg/ml ampicillin), which was then incubated overnight with shaking at 37° C. The resulting culture was pelleted by centrifugation at 10,000×g for 10 minutes and then resuspended in 10 ml LB (with 100 μg/ml ampicillin). The resuspended cells were divided between two 4 l flasks, each containing 750 ml of LB (with 100 μg/ml ampicillin). The cultures were incubated at 37° C. until the cultures reached an optical density of 0.3, isopropylthiogalactoside (IPTG) was added (final IPTG concentration of 1 mM), and the cultures were incubated with shaking for another 3 hours. The cells were harvested by centrifugation at 10,000×g for 10 minutes, washed with buffer I (i.e., containing 50 mM Tris-HCl and 10 mM dithiothreitol at pH 8), and stored as a cell pellet at −80° C.

The cells were thawed and suspended in 50 ml in buffer II (i.e., containing 50 mM Tris-HCl, 5 mM dithiothreitol, 10 mM EDTA, and 0.04 mg/ml lysozyme at pH 8.0). The cell suspension was sonicated on ice three times (for 1 minute each time, 3 minutes between each sonication). The sonicated suspension was centrifuged at 39,000×g for one hour and the supernatant was brought to 1.5 M ammonium sulfate by addition of solid ammonium sulfate with stirring at 4° C. for 30 minutes. The solution was loaded onto a 1.6 cm×14 cm butyl-sepharose fast flow resin (Pharmacia 17-0980-01) packed in an XK16/20 column (Pharmacia 18–8773-01) at a flow rate of 0.5 ml/min. Once loaded onto the resin, the protein was eluted using a fast protein liquid chromatography (FPLC) component system (Pharmacia) at 0.5 ml/min flow rate using 150 ml of the following buffer compositions:

0 to 40 ml: 50 mM Tris-HCl, 5 mM dithiothreitol, pH 8, and 1.5 M ammonium sulfate;

40 to 100 ml: gradient from 1.5 M to 0 M ammonium sulfate in buffer I; and 100 to 150 ml: buffer I.

MurA eluted from the column in fractions collected between 65 and 110 ml.

The eluted MurA was dialyzed against two changes of 4 l of buffer I at 4° C. over 24 hours in 32 mm dialysis tubing (molecular weight cutoff 6000 to 8000; Fisher 08-670D).

The dialyzed MurA was then loaded onto a 1.6 cm×7 cm Source 30Q anion exchange resin (Pharmacia 17-1275-99) packed into an XK16/20 column (Pharmacia 18-8773-01) at a flow rate of 1.0 ml/min. Once loaded onto the resin, the protein was eluted using the FPLC system at a 2 ml/min flow rate using 350 ml of the following buffer compositions:

0 to 150 ml: buffer I;
150 to 350 ml: gradient from 0 M to 1 M potassium chloride in buffer I.

MurA eluted from the column in fractions collected between 18 and 33 ml.

The enzyme was then stored at −80° C. in 220 µl aliquots (protein concentration of about 1.5 mg/ml) in 50 mM Tris-HCl and 150 mM potassium chloride.

Assay: 15 µl samples of solutions containing compounds to be assayed (25 µg/ml) in 50 mM HEPES pH 7.5 were loaded into a 96 well plate. As controls and blanks, 15 µl of the 50 mM HEPES pH 7.5 (i.e., without any compounds to be assayed) was added to certain other wells. 10 µl of enzyme dilution buffer (0.5 ml 1 M Tris-HCl pH 8.0, 50 µl 1 M dithiothreitol, 1.5 µl 0.1 M UDP-GlcNAc, 2 ml glycerol, and distilled water to make 10 ml solution) was added to all of the wells (i.e., sample, control, and blank) to dissolve the compounds. 40 µl diluted MurA (1 µl of a 1.5 mg/ml MurA sample in 5 ml of the above enzyme dilution buffer) was added to all sample and control wells. An additional 40 µl of the enzyme dilution buffer was added to the blank wells. After 10 minutes, 50 µl of reaction buffer (2.5 ml 1 M Tris-HCl pH 8.0, 500 µl 1 M dithiothreitol, 150 µl 0.1 M phosphoenolpyruvate, 150 µl 0.1 M UDP-GlcNAc, and distilled water to make 50 ml solution).

To obtain initial absorbance values ($A_{650}$init) and to check for interference, the plate was read immediately at 650 nm. The plate was then incubated for 60 minutes at room temperature, after which time the reactions were stopped and developed by addition of 190 µl malachite green (MG) solution (0.034% MG in 4.2% ammonium molybdate in 4 N HCl). Final absorbance readings ($A_{650}$final) were taken at 650 nm. The percentage inhibition was calculated according to the following formula:

$$\% \text{ inhibition} = \frac{(\Delta A_{650}\text{control} - \Delta A_{650}\text{sample})}{(\Delta A_{650}\text{control} - \Delta A_{650}\text{blank})} * 100$$

where, for example, $\Delta A_{650}$sample=($A_{650}$final−$A_{650}$init).

A hit in this assay is defined as a compound that exhibits at least 50% inhibition.

Example 5
MurB Biochemical Assay

A UDP-N-Acetylenolpyruvylglucosamine reductase (MurB) biochemical assay that utilizes NADPH to reduce the enolpyruvyl group of UDP-N-acetylglucosamine enolpyruvate to the lactyl ether to make UDP-N-acetylmuramic acid (Benson et al., *Biochemistry*, 32:2024–2030, 1993) was used to follow up on the induction screen of Example 1. The spectrophotometric assay was based on the consumption of NADPH and followed decreasing absorbance at 340 nm.

A MurA batch reaction was carried out to obtain the substrate for the MurB assay: 2 ml 1 M Tris-HCl pH 8.0, 4 ml 0.1 M UDP-GlcNAc, 4 ml 0.1 M phosphoenolpyruvate, 200 µl 1 M dithiothreitol, 20 µl MurA stock (1.5 mg/ml), and 29.8 ml distilled water were combined and incubated overnight at room temperature. 0.5 ml of the reaction solution was then combined with 0.5 ml 1 M Tris-HCl pH 8.0, 7 µl β-mercaptoethanol, 80 µl potassium chloride, 133 µl NADPH, and 8.78 ml distilled water to form a reaction buffer.

A 1.4 mg/ml MurB stock solution was diluted 1:3000 in an ice-cold Tris-BME solution (i.e., 2.5 ml 1 M Tris-HCl pH 8.0, 17.5 µl β-mercaptoethanol, and 50 ml distilled water).

25 µl samples of solutions containing compounds (25 µg/ml) to be assayed in 50 mM HEPES pH 7.5 were loaded into the wells of a 96 well plate. As controls and blanks, 15 µl of the 50 mM HEPES pH 7.5 (i.e., without any compounds to be assayed) was added to certain other wells. 10 µl dimethylsulfoxide was added to each well, followed by 25 µl ice cold Tris-BME solution. 15 µl of the 1:3000 MurB dilution was added to all of the sample and control wells, while 15 µl ice cold Tris-BME solution was added to the blank wells. The plates were incubated at room temperature for 5 minutes, then 50 µl of the reaction buffer described above was added to all of the wells.

The plate was read continuously at 340 nm for 10 minutes to monitor the decrease in absorption. The rate of reaction (in mOD/min) was given by the slope of the line fit to a graph of absorbance (at 340 nm) plotted against time in minutes.

The percentage inhibition was calculated according to the following formula:

$$\% \text{ inhibition} = (SR-CR)/(CR-BR)*100$$

where SR is the rate corresponding to the sample, CR is the control rate, and BR is the background rate.

To rule out false positives (i.e., apparent inhibition) due to compounds that react with $NADP^+$, background readings were collected using 100 µM $NADP^+$ alone in the reaction solution without enzyme or MurA product. A significant rate of increase in absorbance at 340 nm for some samples indicated that a reducing agent was present in those samples. To compensate for the presence of the reducing agent, the rate of increase due to the reducing agent was added to the experimental rate (i.e., SR).

A hit in this assay is defined as a compound that exhibits at least 40% inhibition.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a candidate compound that inhibits bacterial growth, the method comprising:
    contacting bacteria carrying a β-lactamase promoter operably linked to a heterologous reporter gene with the candidate compound to form a reaction mixture; and
    assaying the reaction mixture for induction of expression of the heterologous reporter gene, wherein induction of expression of the heterologous reporter gene indicates that the candidate compound is an inhibitor of bacterial growth.

2. A method of claim 1, wherein the candidate compound is a member of a library of potential inhibitors.

3. A method of claim 1, wherein the assaying step comprises measuring the optical absorbance of the reaction mixture.

4. A method of claim 1, wherein the assaying step comprises detecting the binding of antibodies to a product of the heterologous reporter gene.

5. A method of claim 1, wherein the assaying step comprises detecting mRNA expressed from the heterologous reporter gene.

6. A method for identifying an inhibitor of cell wall biosynthesis, the method comprising:

contacting bacteria carrying a β-lactamase promoter operably linked to a heterologous reporter gene with a candidate compound to form a reaction mixture; and assaying the reaction mixture for induction of expression of the heterologous reporter gene, wherein induction of expression of the heterologous reporter gene indicates that the candidate compound is an inhibitor of cell wall biosynthesis.

7. A method for identifying a candidate compound that can be used to treat infection in an organism by a bacteria, the method comprising:

contacting bacteria carrying a β-lactamase promoter operably linked to a heterologous reporter gene with the candidate compound to form a reaction mixture; and assaying the reaction mixture for induction of expression of the heterologous reporter gene, wherein induction of expression of the heterologous reporter gene indicates that the candidate compound can be used to treat infection.

8. A method of claim 7, wherein the candidate compound is a member of a library of potential inhibitors.

9. A method of claim 7, wherein the organism is a mammal.

10. A method of claim 7, wherein the organism is a human.

11. A method for identifying a candidate compound that inhibits bacterial growth, the method comprising:

providing bacteria carrying a β-lactamase promoter operably linked to a heterologous reporter gene;

incubating the bacteria with the candidate compound, under conditions that enable cell wall biosynthesis, to form a reaction mixture; and assaying for induction of expression of the heterologous reporter gene, wherein induction of expression of the heterologous reporter gene indicates that the candidate compound is an inhibitor of bacterial growth.

12. A method of claim 11, wherein the candidate compound is a member of a library of potential inhibitors.

13. A method of claim 11, wherein the assaying step comprises measuring the optical absorbance of the reaction mixture containing the candidate compound.

14. A method of claim 11, wherein the assaying step comprises detecting the binding of antibodies to a product of the heterologous reporter gene.

15. A method of claim 11, wherein the β-lactamase promoter is a β-lactamase promoter from a bacterial species selected from the group of genera consisting of Citrobacter, Enterobacter, Serratia, Pseudomonas, and Proteus.

16. A method of claim 15, wherein the β-lactamase promoter is a promoter of the ampC gene from *Citrobacter freundii*.

17. A method of claim 11, wherein the reporter gene is lacz.

18. A method of claim 11, wherein the reporter gene is luc.

19. The method of claim 1, wherein the reporter gene is lacZ.

20. The method of claim 1, wherein the reporter gene is luc.

* * * * *